(12) United States Patent
Oren et al.

(10) Patent No.: US 8,118,814 B2
(45) Date of Patent: Feb. 21, 2012

(54) IMPLEMENT FOR ORIENTATING A TOOL, PARTICULARLY USEFUL IN SURGICAL TOOLS FOR HARVESTING AND IMPLANTING BONE PLUGS TO REPAIR DAMAGED BONE TISSUE

(75) Inventors: Ran Oren, Kibbutz Gaaton-Doar-Na Oshrat (IL); F. Alan Barber, Plano, TX (US); Yaron Fuerst, Kfar-Vradim (IL); Dan Moor, Kibbutz Gaaton-Doar-Na Oshrat (IL)

(73) Assignee: DePuy Mitek Inc., Raynham, MA (US)

( * ) Notice: Subject to any disclaimer, the term of this patent is extended or adjusted under 35 U.S.C. 154(b) by 1254 days.

(21) Appl. No.: 11/705,745

(22) Filed: Feb. 14, 2007

(65) Prior Publication Data

US 2008/0195115 A1 Aug. 14, 2008

(51) Int. Cl.
*A61B 17/56* (2006.01)
*B25B 33/00* (2006.01)

(52) U.S. Cl. ......................................................... 606/96
(58) Field of Classification Search .............. 606/79–85, 606/96–100, 102–104, 86 R
See application file for complete search history.

(56) References Cited

U.S. PATENT DOCUMENTS

| | | | | |
|---|---|---|---|---|
| 4,821,716 | A | * | 4/1989 | Ghajar et al. ................. 606/172 |
| 5,111,929 | A | * | 5/1992 | Pierick et al. ................. 198/495 |
| 5,197,967 | A | * | 3/1993 | Wilson ............................ 606/79 |
| 5,331,972 | A | * | 7/1994 | Wadhwani et al. ........... 600/567 |
| 5,712,727 | A | * | 1/1998 | Mouri ............................ 359/431 |
| 5,782,835 | A | | 7/1998 | Hart et al. |
| 5,891,085 | A | * | 4/1999 | Lilley et al. ..................... 604/68 |
| 5,919,196 | A | | 7/1999 | Bobic et al. |
| 5,993,453 | A | * | 11/1999 | Bullara et al. ................. 606/79 |
| 6,001,567 | A | * | 12/1999 | Brow et al. ........................ 435/6 |
| 6,017,348 | A | | 1/2000 | Hart et al. |

(Continued)

FOREIGN PATENT DOCUMENTS

WO WO 2008/099381 8/2008

OTHER PUBLICATIONS international Search Report Dated Oct. 23, 2008 From the International Searching Authority Re.: Application No. PCT/IL2008/000148.
Written Opinion Dated Oct. 23, 2008 From the International Searching Authority Re.: Application No. PCT/IL2008/000148.
Invitation to Pay Additional Fees Dated Aug. 8, 2008 From the International Searching Authority Re.: Application No. PCT/IL2008/000148.

(Continued)

*Primary Examiner* — Thomas C. Barrett
*Assistant Examiner* — Christopher Beccia

(57) ABSTRACT

An implement for orientating a tool at a predetermined angle with respect to a plane of a target surface to be engaged by the tool includes a rod having a distal end coupled to a head formed with three contact points arranged in a circular array around the longitudinal axis of the rod, such that the three contact points define a plane. The rod is coupled to the head with the longitudinal axis of the rod at the predetermined angle to the plane defined by the three contact points, such that when the three contact points of the rod are in contact with the target surface, the longitudinal axis of the rod is at the predetermined angle with respect to the plane of the target surface. The implement is described particularly for orientating a surgical cutting tool perpendicularly to bone tissue for harvesting and implanting a bone plug to repair damaged bone tissue.

18 Claims, 7 Drawing Sheets

U.S. PATENT DOCUMENTS

| | | | | |
|---|---|---|---|---|
| 6,146,385 | A * | 11/2000 | Torrie et al. | 606/96 |
| 6,306,142 | B1 | 10/2001 | Johanson et al. | |
| 6,395,011 | B1 | 5/2002 | Johanson et al. | |
| 6,592,588 | B1 * | 7/2003 | Bobic et al. | 606/79 |
| 6,767,354 | B2 * | 7/2004 | Johanson et al. | 606/179 |
| 6,942,669 | B2 * | 9/2005 | Kurc | 606/80 |
| 7,401,435 | B1 * | 7/2008 | Ryan | 43/57.1 |
| 7,497,861 | B2 * | 3/2009 | Bharadwaj et al. | 606/84 |
| 2003/0163118 | A1 * | 8/2003 | Hamilton et al. | 604/525 |
| 2004/0167527 | A1 * | 8/2004 | Simon et al. | 606/79 |
| 2006/0009774 | A1 * | 1/2006 | Goble et al. | 606/85 |

OTHER PUBLICATIONS

International Preliminary Report on Patentability Dated Jan. 21, 2010 From the International Bureau of WIPO Re.: Application No. PCT/IL2008/000148.

Official Action Dated Jul. 23, 2009 From the US Patent and Trademark Office Re.: U.S. Appl. No. 11/705,745.

International Preliminary Report on Patentability Dated Sep. 22, 2010 From the International Preliminary Examining Authority Re. Application No. PCT/IL08/00148.

* cited by examiner

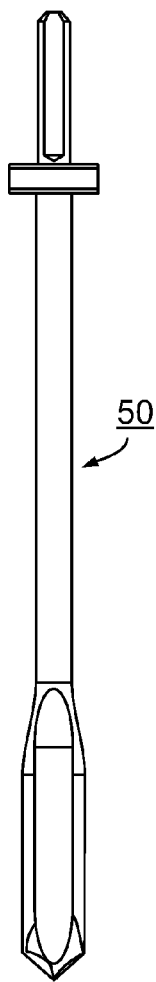
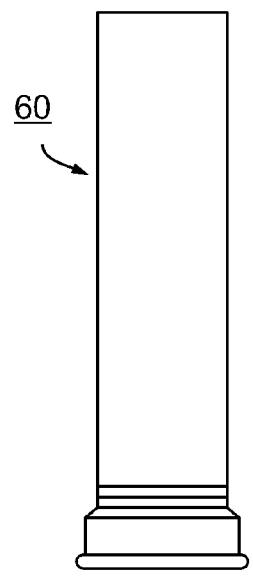
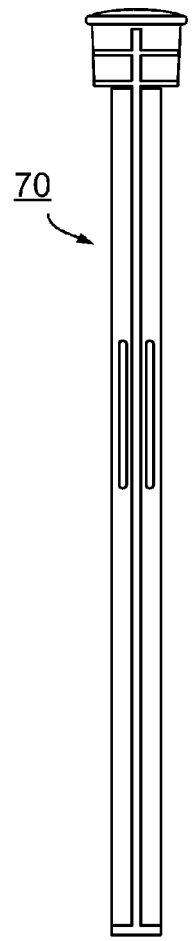
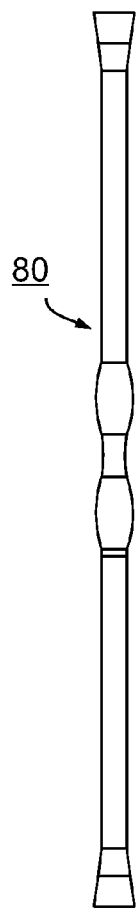
Fig. 8d    Fig. 8e    Fig. 8f    Fig. 8g
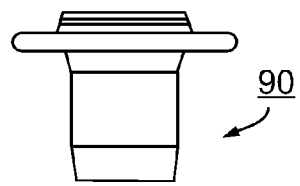
Fig. 8h

IMPLEMENT FOR ORIENTATING A TOOL, PARTICULARLY USEFUL IN SURGICAL TOOLS FOR HARVESTING AND IMPLANTING BONE PLUGS TO REPAIR DAMAGED BONE TISSUE

FIELD AND BACKGROUND OF THE INVENTION

The present invention relates to an implement for orientating a tool at a predetermined angle with respect to a target surface to be engaged by the tool. The invention is particularly useful in surgical tools for harvesting and implanting bone plugs to repair damaged bone tissue, and is therefore described below with respect to such an application, but it will be appreciated the invention can be used in other applications. The invention also relates to a method of harvesting and implanting bone plugs to repair damaged bone tissue.

The surfaces of the bones in a sinovial joint, such as the knee, have protective covers made up of articular cartilage. The cartilage optimizes weight distribution over the joint surface, minimizes friction and wear, and allows for a smooth glide over the joint surface with motion. Beneath this protective cover of articular cartilage lies a layer of subchondral bone, followed by cancellous bone.

A defect in, or damage to, the cartilage will cause local irritation, producing pain and swelling. In patients with a disease known as osteochondritis dissecans (OCD), there is a localized full osteocartilaginous separation at the level of the subchondral bone that can damage the protective cover. Unless the lesion repairs itself or is treated, the disease will progress. OCD lesions may occur in any joint, but they occur most often in the knee and the ankle.

The treatment of all cartilage lesions depends on the patient's age and the extent of the lesion. Treatment options for patients first manifesting symptoms of such lesions may include non-surgical treatment or surgical treatment. Young people usually respond well to non-surgical treatment. However, adults generally require at least diagnostic arthroscopy to evaluate the lesion, and frequently also surgical intervention to treat it. Surgical procedures to treat the lesions include open or arthroscopic drilling, debridement, reduction and fixation with pins or screws, bone grafting, chondrocyte implantation and osteochondral grafts.

Surgical techniques for autologous osteochondral grafting involve transplanting bone plugs. This typically involves removing the damaged bone tissue by drilling or cutting a hole at the site of the damage (the recipient site), and filling this hole with a bone plug with its cartilage layer as harvested or extracted from healthy tissue in non-load-bearing joint surfaces in the patient's body (the donor site).

Surgical instruments are currently available which may be used to harvest or extract a bone plug from a donor site and then to implant it into a pre-formed hole at the recipient site. A conventional harvesting instrument typically includes a tube having a cutting edge at the distal end. To extract a plug, the tube is driven into the bone at the donor site and then removed, taking with it a plug of healthy bone tissue. The plug is then generally transferred to a delivery device for implantation at the receiving site. Examples of methods and devices for harvesting and implanting bone plugs are described in U.S. Pat. Nos. 6,767,354, 6,395,011, 6,306,142, 6,017,348, 5,919,196 and 5,782,835.

The success of grafting (implanting) depends on, among other factors, the fit in size and shape of the harvested graft (bone plug) to the hole formed at the receiving site. Perpendicularity of the harvesting and of the drilling operations is essential in order to achieve a good fit between the layers of the graft and of the receiving site.

Several devices and systems are currently in use for performing osteochondral grafting. However, they generally do not include means to establish perpendicularity of the harvested plug, but rather rely on visual estimation only. In procedures performed arthroscopically, the narrow field of vision makes visual assessment difficult and not sufficiently accurate for this purpose.

Another drawback of most available devices and systems is that they require the transfer from the harvester into a separate delivery device, or require the application of a delivery sheath over the harvester tube (e.g., see for example the above-cited U.S. Pat. No. 6,767,354). Transferring the graft from one tube to another presents a serious hazard to graft integrity as it can lead to the separation of the cartilage layer from the bone plug. Transferring the graft from the harvester tube via a delivery sheath, as in U.S. Pat. No. 6,767,354, is generally done by mallet blows on the proximal face of the plug, and therefore also involves a grave hazard of separation of the cartilage from the bone because of the friction between the plug and the wall of the delivery sheath.

It will appreciated that while the invention is particularly useful in surgical operations for harvesting bone plugs, the invention may also be used in many other applications, for example in drilling holes through workpieces at a precise predetermined angle to the workpiece surface, particularly where the viewing of the workpiece surface is obstructed or limited.

OBJECTS AND BRIEF SUMMARY OF THE PRESENT INVENTION

An object of the present invention is to provide an implement for orientating a tool at a predetermined angle with respect to a target surface to be engaged by the tool. Another object of the invention is to provide a surgical implement having advantages in one or more of the above respects for harvesting and implanting bone plugs. A further object of the invention is to provide a method for harvesting and implanting bone plugs also according advantages in one or more of the above respects.

According to a broad aspect of the present invention, there is provided an implement for orientating a tool at a predetermined angle with respect to a plane of a target surface to be engaged by the tool, the implement comprising: a rod having a longitudinal axis, a proximal end, and a distal end; and a head coupled to the distal end of the rod; the head being formed with three contact elements arranged in a circular array around the longitudinal axis of the rod; the head being formed with three contact elements arrayed in a circular array around the longitudinal axis and radially displaceable from inner positions to outer positions with respect to each other and to the longitudinal axis such that when in their outer positions either tips are in contact with the target surface at three contact points which define a plane on the target surface at the predetermined angle to the longitudinal axis of the rod; the contact elements being formed by three slits extending axially through the distal end of the head for a sufficient distance to enable the contact elements to be elastically deformed to the inner and outer positions; the rod being coupled to the head so as to be displaceable with respect thereto to radially displace the three contact elements to their outer positions.

According to a more specific aspect of the present invention, there is provided a surgical implement comprising: a surgical tool including a tube to be oriented at a predetermined angle with respect to a plane of a target surface to be engaged by the tool; a rod located within the tube and of smaller outer diameter than the inner diameter of the tube; the rod having a longitudinal axis coaxial with that of the tube, a distal end to be disposed within the end of the tube to engage the target surface, and a proximal end to project outwardly of the opposite end of the tube; and a head coupled to the distal end of the rod; the head being formed with three contact elements arrayed in a circular array around the longitudinal axis and radially displaceable from inner positions to outer positions with respect to each other and to the longitudinal axis such that when in their outer positions, their tips are in contact with the target surface at three contact points which define a plane on the target surface at the predetermined angle to the longitudinal axis of the rod; the contact elements being formed by three slits extending axially through the distal end of the head for a sufficient distance to enable the contact elements to be elastically deformed to the inner and outer positions; the tube being displaceable to either a first position wherein the distal end of its inner surface engages the outer surfaces of the contact elements to retain the contact elements in their inner positions, or to a second position wherein the digital end of its inner surface disengages from the outer surfaces of the contact elements to permit the contact elements to move to their outer positions; the rod being coupled to the head so as to be displaceable with respect thereto to radially displace the three contact elements to their outer positions.

In most applications of the invention, the predetermined angle would be 90°, such that the longitudinal axis of the rod would be precisely perpendicular to the plane of the target surface. In some applications, however, the predetermined angle may be other than 90°.

According to further features in the described preferred embodiment, the length of the rod from the distal end to its proximal end is many times the diameter of the circular array of three contact points, thereby multiplying by many times any deviation of the proximal end of the surgical tool with respect to the predetermined angle.

As will be described more particularly below, an implement for orientating a tool, particularly a surgical tool, constructed in accordance with the foregoing features enables the surgical tool to be precisely oriented at the desired angle (usually perpendicularly) with respect to the target surface to be engaged by the tool, even though the view of the target surface is very limited or obstructed.

According to another aspect of the present invention, there is provided a method of harvesting a bone plug from a donor site and implanting it in a recipient site by using the above-defined apparatus.

As will be described below, such a method has a number of advantages over existing methods, in that it eliminates the need to transfer the bone plug from the harvester device into a separate delivery device, or to apply a separate delivery device to the harvester device. Moreover, as the harvested bone plug lies distal to the integral delivery section of the harvesting device, the plug is transferred into the delivery section cartilage layer first, i.e. opposite to the direction of transfer in predicate devices, thereby reducing the hazard of cartilage separation or damage. In addition, the transparent section of the tubular cutting tool, since it is used only for temporarily retaining the plug until the tool is transferred to the recipient site, may be of slightly larger diameter than the cutting section formed with the sharp cutting edge, such that relatively little force is needed for transferring the plug from the transparent section to the bore at the recipient site, thereby further reducing the hazard of cartilage separation or damage.

Further features and advantages of the invention will be apparent from the description below.

BRIEF DESCRIPTION OF THE DRAWINGS

The invention is herein described, by way of example only, with reference to the enclosed drawings, wherein

FIGS. 8a-8i illustrate the contents of a surgical kit that may be provided for harvesting and implanting bone plugs in accordance with the present invention.

It is to be understood that the foregoing drawings, and the description below, are provided primarily for purposes of facilitating understanding the conceptual aspects of the invention and possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF A PREFERRED EMBODIMENT

Figure 1:
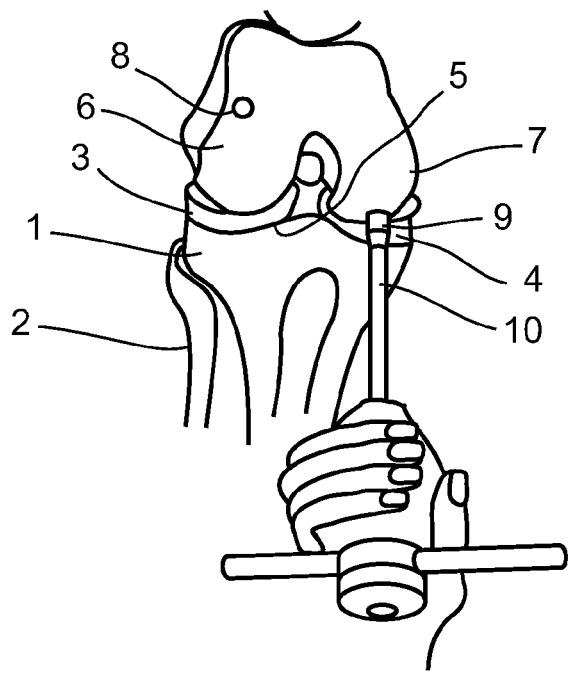
FIG. 1 is a schematic illustration of a knee joint, and of a osteochondral grafting procedure applied thereto for harvesting a bone plug from a donor site of the knee joint and implanting it in a recipient site in order to repair damaged bone tissue at the recipient site.
Figure 2:
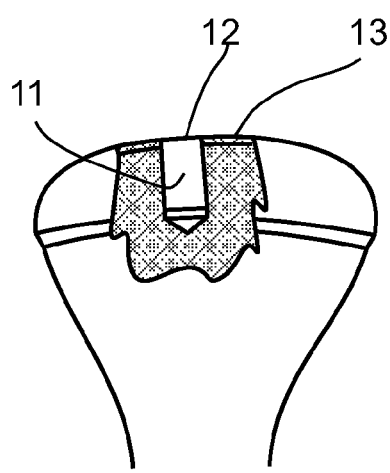
FIG. 2 illustrates a bone plug after transplantation from the donor site to the recipient site.
Figure 3:
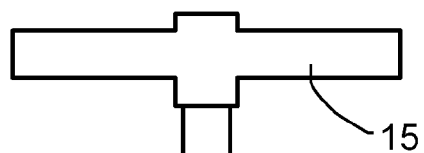
FIG. 3 is a side elevational view illustrating a harvesting device used for harvesting a bone plug from a donor site.

The Overall Osteochrondal Graft Procedure (FIGS. 1-3)

For purposes of example, the preferred embodiment of the invention described below is an osteochrondral graft procedure. Such a procedure involves the treatment of a cartilage lesion in a patient's knee in order to repair damaged bone tissue at a donor site therein by harvesting a bone plug from healthy bone tissue at a donor site in a non-load-bearing joint surface in the patient's body, and implanting the bone plug in a bore formed in the damaged bone tissue at the recipient site of the patient's body. The procedure includes the following main steps:

1. Opening portals for visualization, irrigation and accommodation of the instrument;

2. Assessing the area of the lesion and determining the number and size of bone grafts (bone plugs) needed to cover the entire damaged area, starting adjacent to healthy bone;

3. Harvesting from the donor site a perpendicular bone plug suitable for implantation;

4. Drilling a bore at the damaged bone site perpendicular to the bone surface;

5. Introducing the harvested plug into the bore drilled in the recipient site, with the surface of the bone plug matching the surface of the bone at the recipient site;

6. Repeating steps 3-5 for additional grafts if needed to cover the entire damaged area; and 7. Withdrawing the instruments and closing the portals.

The present invention concerns primarily steps 3, 4 and 5 in the above surgical procedure, to assure that these steps are performed while the surgical instrument involved is precisely perpendicular to the outer surface of the bone tissue being acted upon, even though the view of the treatment site is very limited or obstructed.

FIG. 1 illustrates the knee in about 30° flexion. The leg bones, the tibia 1 and the fibula 2, are shown with the menisci, lateral 3 and medial 4, on the tibial plateau contacting the lateral 6 and medial 7 condyles of the femur. The knee cap has been lifted to allow access to the joint. A cylindrical bone plug (graft) has been removed from the donor site 8 on the upper part of the lateral condyle and is to be grafted into a hole pre-drilled at the recipient site 9 in the medial condyle. The graft is both harvested from the donor site, and implanted in the recipient site, by a harvesting tool generally designated 10.

FIG. 2 shows the implanted graft 11, and particularly the required match between the cartilage of the graft 12 and that of the recipient bone 13.

FIG. 3 shows a surgical tool heretofore used for harvesting the graft. Such a tool includes a tube 14 having a handle 15 at its proximal end to facilitate manual rotation of the tube. The distal end 16 of tube 14 is chamfered on the outside and beveled on the inside to form a sharp cutting edge for easier penetration into the donor bone. After harvesting, the plug is generally transferred into a separate device for implantation at the recipient site.

The Novel Surgical Tool (FIGS. 4-7)

Figure 4:
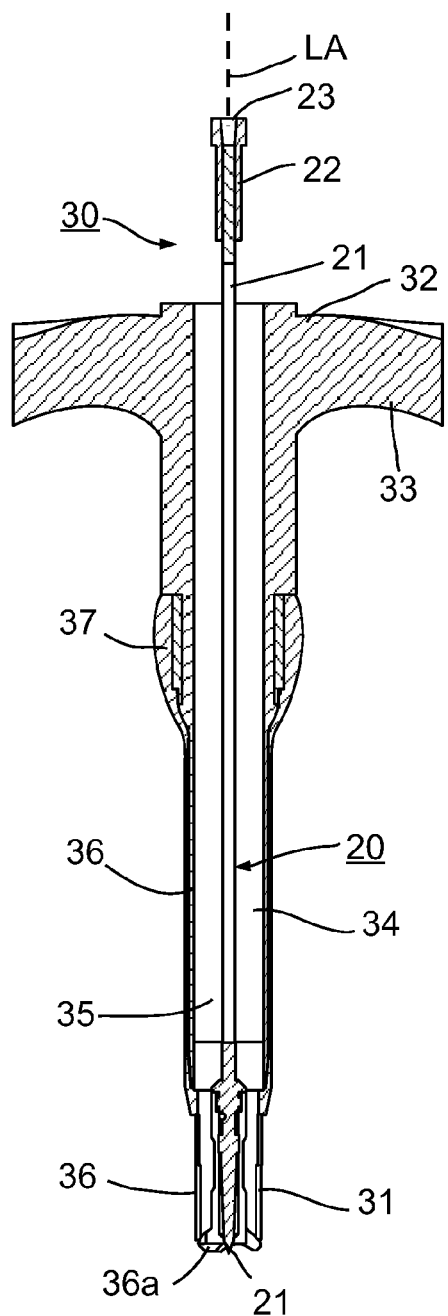
FIG. 4 is a longitudinal sectional view illustrating a surgical instrument constructed in accordance with the present invention for use in both harvesting a bone plug at a donor site and implanting it in the recipient site.
Figure 5:
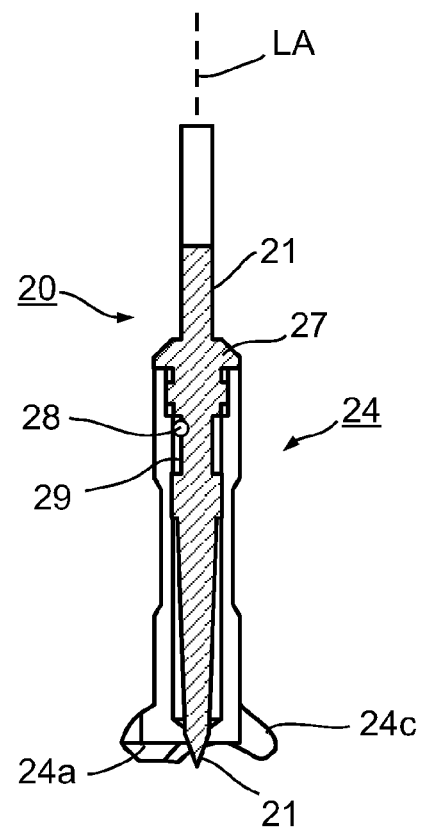
FIG. 5 is an enlarged sectional view illustrating only the orientation implement in the surgical instrument of FIG. 4.

FIG. 4 illustrates a novel surgical cutting tool constructed in accordance with the present invention for harvesting a bone plug from a donor site and also for implanting the harvested plug in a bore formed in the recipient site to replace damaged tissue at the recipient site. The illustrated surgical tool includes a novel orientation implement which better assures orientating the surgical cutter tool so as to be precisely perpendicular to the plane defined by the outer surface of the bone tissue at the both the donor site and at the recipient site. FIG. 5 illustrates the orientation implement alone, wherein it is generally designated 20; whereas FIG. 4 illustrates the orientation implement 20 within the surgical tool, therein generally designated 30. In the example illustrated in FIG. 4, the surgical tool 30 is used for both harvesting a bone plug from a donor site, and for implanting the harvested bone plug in the recipient site without transferring the bone plug to another instrument.

As shown particularly in FIG. 4, the orientation implement 20 includes an elongated rod 21 having a distal end 21a formed with a pointed distal tip 21b to be located within the distal end 31 of the surgical cutter tool to engage the bone tissue, and a proximal end 22 to project outwardly of the proximal end 32 of the surgical tool. The proximal end 32 of the surgical cutter tool includes a handle 33 to facilitate rotating the tool while under pressure, and the proximal end 22 of the orientation rod 20 also includes a handle 23 for manipulating it within the surgical cutter tool.

Figure 6:
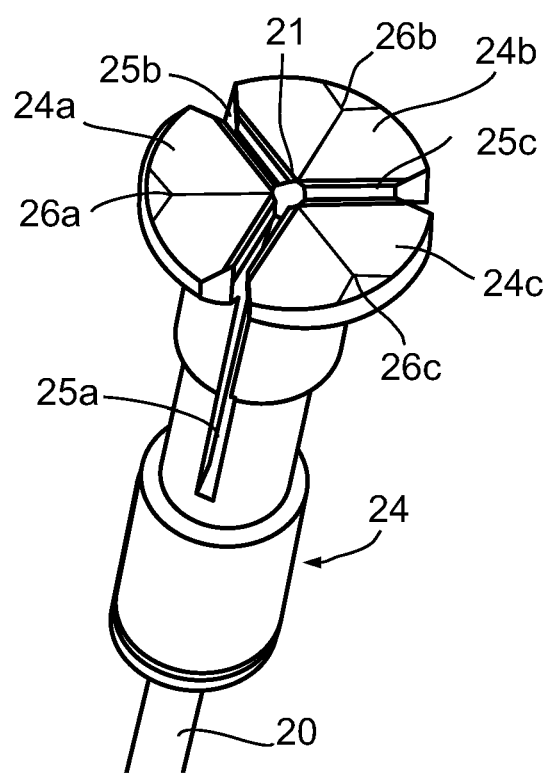
FIG. 6 is a perspective view of the distal end of the orientation implement of FIG. 5.
Figure 7:
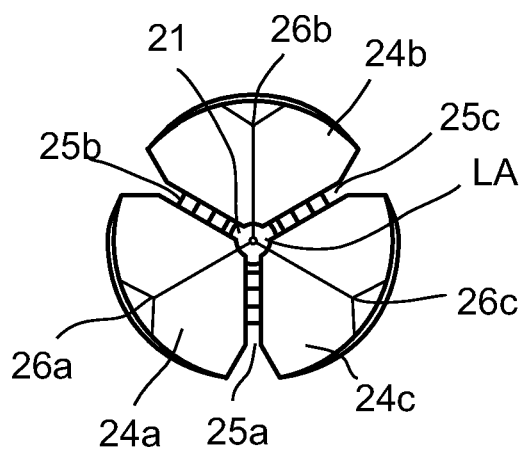
FIG. 7 is an end view of the distal end of the orientation implement of FIG. 5.
Figure 8A:
Figure 8B:
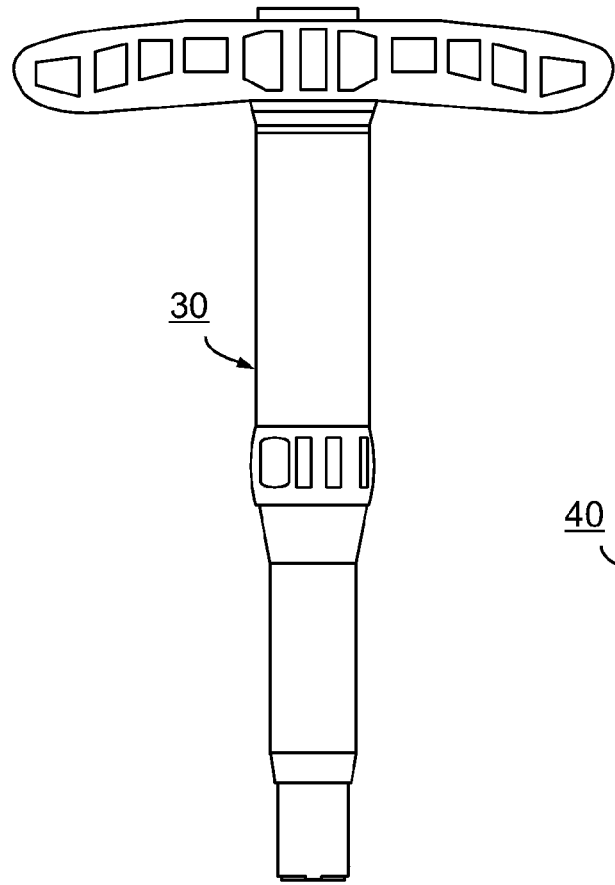
Figure 8C:
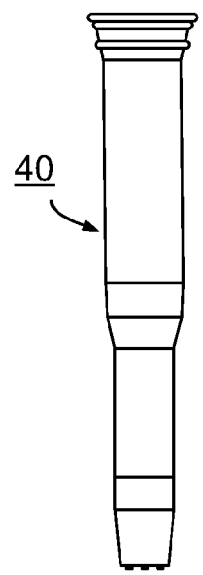
Figure 8I:
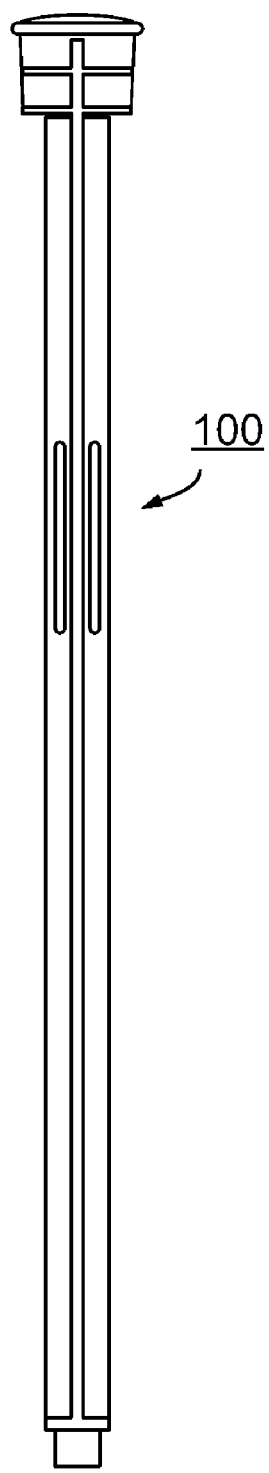

As shown particularly in FIGS. 6 and 7, orientation rod 20 is coupled, at its distal end 21a, to a head 24 formed with three segmental elements 24a-24c defined by three slits 25a-25c formed in a Y-configuration and extending from the distal end of the head to a point short of its proximal end, as shown particularly in FIG. 6. As shown in FIGS. 6 and 7, the three slits 25a-25c intersect at the longitudinal axis of the orientation rod 20. They enable the three segmental elements 24a-24c of head 24 to be elastically deformable to a non-expanded condition, as illustrated in FIG. 4, or to an outwardly-expanded condition as illustrated in FIGS. 5-7. The three segmental elements 24a-24c are normally in their expanded condition (FIGS. 5-7), but are elastically deformable to their non-expanded condition when enclosed within surgical tool 30 (as shown in FIG. 4).

Each of the three segmental elements 24a-24c are formed at their distal ends with a plurality of flat faces such as to define a contact point 26a-26c, respectively. When the segmental elements are in their expanded condition (FIGS. 6 and 7), the three contact points 26a-26c are disposed in a circular array around the longitudinal axis LA of orientation rod 20 and lie in a plane perpendicular to the longitudinal axis of the orientation rod.

It will thus be seen that, when the three contact points 26a-26c are in firm contact with the bone tissue to be engaged by the surgical tool 30, the longitudinal axis LA of orientation rod 20 is precisely perpendicular to the plane of the contacted tissue; and when the proximal end 22 of orientation rod 20 is precisely centered with respect to the proximal end 32 of the surgical tool, the distal end of the surgical tool is also precisely oriented perpendicularly to the plane of the contacted tissue.

As indicated earlier, surgical cutter tool 30 is of tubular configuration. It includes a central passageway 34 having a diameter substantially larger than the outer diameter of orientation rod 20 so as permit the rod and its head 24, to be received within that passageway, with the three segmental elements 24a-24c in their closed, non-expanded condition, as shown in FIG. 4.

The distal end of surgical cutter tool 30 includes a transparent section 35 of optically transparent material. The surgical tool further includes a cutter section 36 formed at its distal end with a sharp circular cutting edge 36a. Cutter section 36 is defined by a separate cutter unit which has an inner diameter substantially equal to the outer diameter of the transparent section 35 of the cutter tool 30 so as to be snugly receivable thereover. The proximal end of cutter unit 36 includes a quick-coupling 37 for quickly coupling the cutter unit 36 to transparent section 35. The quick coupling is located at the mid section of the transparent section 35 and at the proximal end of the tubular cutter unit 36.

The proximal end of the surgical tool is further formed with the above-mentioned handle 33 to facilitate rotating the surgical tool, while pressing cutting edge 36a of the cutter unit against the bone tissue to cut-out a cylindrical plug from the bone tissue.

As shown particularly in FIG. 5, the distal end of orientation rod 20 is formed with an annular shoulder 27 abuttable against the end of head 24, such that moving the rod in the distal direction also moves with it head 24. However, when rod 20 is moved in the proximal direction, a lost-motion coupling is effected between the rod and head 24, by a pin 28 fixed to the head and receivable within a recess 29 in the rod. Thus, when the rod is moved in the proximal direction (i.e., tending to withdraw it from tool 30), the lost-motion coupling defined by pin 28 and recess 29 permits the rod to move a short distance before picking up the head 24 and moving it with the rod in the proximal direction.

The orientation rod 20 is used for orienting the cutter tool 30 precisely perpendicularly to the bone tissue, either at the donor site to extract a bone plug, or at the recipient site to produce the bore for receiving the extracted plug. When so used, rod 20 is pressed in the distal direction such that its shoulder 22 abuts against the proximal end of head 24 to move it in the distal direction, while the pointed tip 21b at the distal end 21a of the rod cams apart the three segmental elements 24a-24c against the inner surface of the cutter edge 36a of the cutter unit 36, such as produce a relatively rigid assembly defining the perpendicular position of the rod 20, and thereby of the cutter tool 30. When the orienting rod is to be removed, it is withdrawn in the proximal direction, whereupon the tapered tip 21b at its distal end first withdraws from contact with the three segmental elements 24a-24c, this being permitted by the lost-motion connection between pin 28 and recess 29. Further withdrawal of the rod through the proximal end of the cutter tube 30 pulls with it the three segmental elements 24a-24c of the head 24. During this movement of elements 24a-24c, they are forced to their closed, non-expanded condition by the inner surface of tube 30, thereby permitting the rod 20 and head 24 to be withdrawn from the cutter tube.

A Kit for Osteochrondral Grafting (FIGS. 8a-8i)

FIGS. 8a-8i illustrate the contents of a surgical kit for use in the above-described osteochrondral grafting procedure. Thus, such a kit includes the orientation rod 20 (FIG. 8a) and the surgical cutter tool 30 (FIG. 8b) as described above.

In addition, the kit further includes a guide tube 40 (FIG. 8c) and a spade drill 50 (FIG. 8d) for drilling a bore at the recipient site. As will be described more particularly below, guide tube 40 is used with the orientation rod 20 for orientating the guide tube perpendicularly to the bone tissue at the donor site; whereupon the orientation rod 20 is removed, and the spade drill 50 (FIG. 9d) is then introduced into the guide tube to drill the bore in the recipient site.

The illustrated kit also includes a transfer tube 60 (FIG. 8e) which is used for transferring a bone plug removed from the donor site by the surgical cutter tool 30 and received within its cutter unit 36, to the transparent section 35 of the surgical tool. As will be described more particularly below, this enables the surgeon to view the delivery of the harvested bone plug into the recipient site during the implanting operation.

The illustrated kit further includes a plunger 70 (FIG. 8f) for transferring the harvested bone plug from the transparent section of the surgical cutter tool 30 into the bore at the recipient site; and a tamping device 80 (FIG. 8g) which may be used for the final setting of the transferred bone plug to the correct depth relative to the cartilage surface at the recipient site.

The illustrated kit further includes a cap 90 (FIG. 8h) which may be applied to the proximal end of the surgical cutter tool 30 to close it during its transfer to the recipient site. At the recipient site, cap 90 would be removed to allow the orientation rod 20 to be introduced and manipulated as described above for determining the perpendicular position of the surgical tool to the plane of the bone tissue at the recipient site to receive the harvested bone plug.

Finally, the illustrated kit also includes an obturator (namely, a removable plug used during the insertion of many tubular instruments) 100 (FIG. 8i) which, if the surgeon prefers not to use the orientation rod 20, may be inserted into the tubular surgical cutter tool 30 to prevent tissue fragments from entering the tubular cutter during the cutting operation.

Preferably, a set of such implements would be provided for each plug size. All components of the kit should be of a suitable biocompatible material as known in the prior art.

The Manner of Use (FIGS. 9a-9g)

The manner of using the novel surgical cutter tool illustrated in FIGS. 4-6 of the drawings, and other implements in the kit illustrated in FIGS. 8a-8i, in an osteochondral grafting procedure, will now be described with reference to FIGS. 9a-9g.

Thus, conventional procedures may be used for performing steps 1 and 2 above, namely for: (1) opening portals for visualization, irrigation and accommodation of the instruments; and (2) for assessing the area of the lesion and determining the number and size of grafts needed to cover the entire damaged area, starting adjacent to healthy bone. The surgical implements illustrated in FIGS. 4-7, and in the kit of FIGS. 8 and 8a, may then be used for performing the remaining steps of the procedure, as follows:

Step 3 is performed by first applying the surgical cutter tool 30 to a donor site of healthy bone tissue for harvesting, from the donor site, a perpendicular bone plug suitable for implantation. This is done by applying the surgical cutter tool 30, together with the orientation rod 20 and its head 24, to the donor site with the three segmental elements 24a-24c of the head in their closed, non-expanded condition as illustrated in FIG. 4, with orientation rod 20 substantially centered within the surgical cutter tool 30, and with the pointed distal tip 21 of orientation rod 20 located substantially at the center of the cylindrical plug to be harvested from the donor site.

Orientation rod 20 is moved in the distal direction of the surgical cutter tool 30 to deploy the three segmental elements 24a-24c of head 24, at the distal end of the rod, to their expanded condition, as illustrated in FIGS. 6 and 7. In this expanded condition their three contact points 26a-26c define a plane which is brought into firm contact with the surface of the bone tissue at the donor site. When this occurs, the longitudinal axis LA of orientation rod 20 is precisely perpendicular to the plane of the bone tissue surface contacted by the three contact points 26a-26c of the segmental elements 24a-24c. The surgical cutter tool 30 may then be manipulated precisely to center the proximal end of orientation rod 20 within passageway 33 of tool 30, thereby assuring that the longitudinal axis of the surgical cutter tool 30, particularly the sharp circular cutter edge 36a of the cutter unit 36, is located precisely perpendicularly to the surface of the bone tissue to be engaged by the cutter edge.

While holding the surgical cutter tool in this position, the orientation rod 20 may be withdrawn via the proximal end 32 of the surgical cutter tool, taking with it, head 24 coupled to the distal end of the rod.

While the surgical cutter tool 30 is located in this perpendicular position, it may be rotated, via its transverse handle 37, to cause the sharp cutting edge 36a of its cutter unit 36 to cut into the bone tissue and to harvest a tubular bone plug therefrom. The so harvested bone plug is received within the cutter unit 36 of the surgical cutter tool 30, so that it now includes, in its cutter section 34, a bone plug harvested from the donor site suitable for implantation in the recipient site.

Figure 9A:
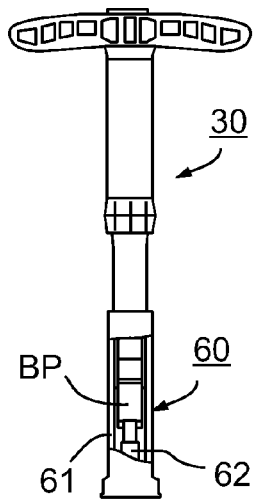
FIGS. 9a-9f illustrate a sequence of operations involved in harvesting a bone plug from a donor site and implanting it in a recipient site using the surgical instrument of FIGS. 4-7, and other implements in the kit of FIGS. 8a-8i.
Figure 9B:
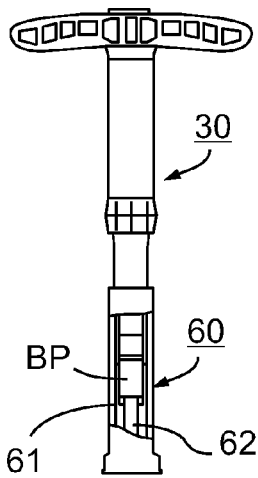
Figure 9C:
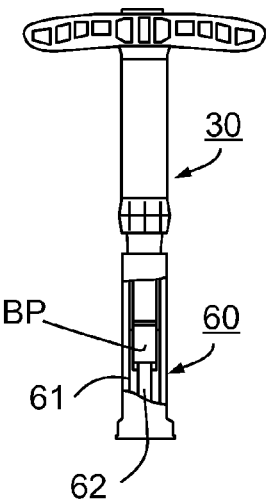

The bone plug within the cutter unit 36 is then transferred to the transparent section 36 of the cutter tool and may thus be viewed by the surgeon. This transfer may be effected by transfer tube 60 illustrated in FIG. 8e. FIGS. 9a-9c illustrate how the transfer tube 60 is effective to transfer the bone plug from the cutter unit 35 of the surgical tool 30 to its transparent section 36.

Figure 9D:
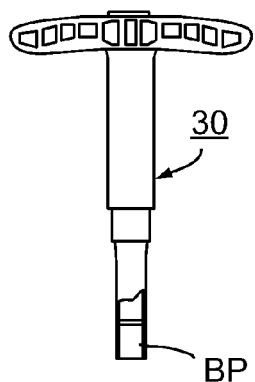

Thus, as shown particularly in FIG. 9a, transfer tube 60 includes an outer wall 61 having an inner diameter substantially equal to the outer diameter of the distal end of the surgical cutter tool 30 so as to be receivable over its distal end and to be slidable therealong towards its proximal end. Transfer tube 60 further includes a central stem 62 of smaller outer diameter than the inner diameter of the distal end of surgical cutter tool 30 so as to be engageable with the bone plug, shown at BP in FIG. 9a, and to move it from the cutter unit 36 into the transparent section 35 of the surgical cutter tool when the transfer tube is pressed inwardly towards the proximal end of that cutter tool, as shown in FIGS. 9b and 9c. Transfer tube 60 is removed from the cutter unit 36, and the cutter unit is then removed via its quick-coupling 37 from the surgical cutter tool 30, leaving the bone plug in the transparent section 35 of the surgical cutter tool 30, as illustrated in FIG. 9d.

Step 4 of the above procedure may now be performed, or may have been performed before step 3. In any event, step 4 is performed by drilling through the damaged bone to produce a recipient bore perpendicular to the surface of the bone tissue. This step is also performed by the use of the orientation rod 20 to assure that the recipient bore so formed is also perpendicular to the surface of the bone tissue.

Thus, for performing this step, guide tube 40 (FIG. 8c) is used with the orientation rod 20 (FIG. 8a) in order to orient the guide tube perpendicularly to the bone tissue to be removed at the recipient site. After the guide tube is so oriented, the orientation rod 20 is removed, and the spade drill 50 (FIG. 8d) is received within the guide tube to drill the bore in the recipient site.

Figure 9E:
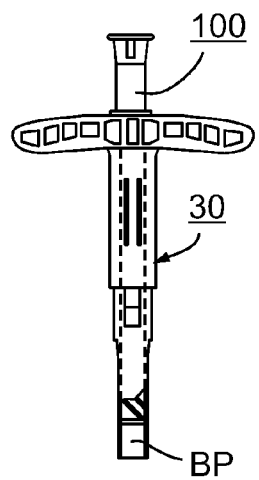
Figure 9F:
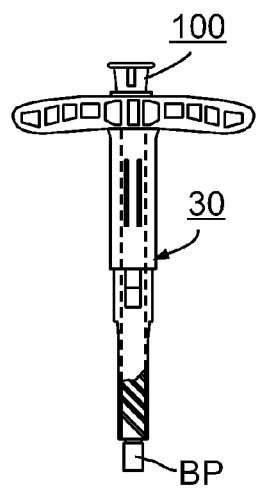

Plunger tube 70 (FIG. 8f) is used for transferring the bone plug BP from the surgical cutter tool 30 into the bore previously formed in the recipient site, as shown in FIGS. 9e and 9f.

As indicated earlier, cap 90 (FIG. 8h) may be applied to the proximal end of the surgical cutter tool 30 to close it during its transfer with the harvested bone plug to the recipient site, whereupon cap 90 would be removed to enable implanting the harvested plug into the bore formed at the recipient site. The transfer of the harvested plug into the bore at the recipient site may be effected by plunger 70 (FIG. 8f) and tamping device 80 (FIG. 8g), the latter being used for the final setting of the transferred bone plug to the correct depth relative to the cartilage surface at the recipient site. Obturator 100 may be used to prevent tissue fragments from entering the surgical cutter tube.

It will be appreciated that the same tubular cutter used for harvesting would not be used for drilling at the recipient site as the outer diameter of the drilling tool must be approximately equal to the inner diameter of the harvesting tool. Accordingly, two tubular cutters with different diameters would be used. Since the orientating device would be dimensioned for a specific tube inner diameter, two orientating devices would be required.

Variations and Other Applications

While the invention has been described with respect to a preferred embodiment for harvesting a bone plug from healthy bone tissue at a donor site and for implanting the harvested bone plug into a bore formed in the recipient site, it will be appreciated that the invention could be used in many other applications. For example, it could be used in drilling bores through workpieces where the bore is to be drilled at a predetermined angle, particularly where viewing the workpiece is limited or obstructed. In addition, while the preferred angle of orientation is 90° with respect to the plane of the target surface, other angles may be desired for particular applications.

Many other variations, modifications and application of the invention will be apparent.

What is claimed is:

1. An implement for orientating a tool at a predetermined angle with respect to a plane of a target surface to be engaged by the tool, said implement comprising:

a rod having a longitudinal axis, a proximal end, and a distal end;

and a head coupled to the distal end of said rod;

said head being formed with three contact elements arranged in a circular array around the longitudinal axis of the rod;

said head being formed with three contact elements arrayed in a circular array around said longitudinal axis and radially displaceable from inner positions to outer positions with respect to each other and to said longitudinal axis such that when in their outer positions either tips are in contact with the target surface at three contact points which define a plane on the target surface at said predetermined angle to said longitudinal axis of the rod;

said contact elements being formed by three slits extending axially through the distal end of the head for a sufficient distance to enable the contact elements to be elastically deformed to said inner and outer positions;

said rod being coupled to said head so as to be displaceable with respect thereto to radially displace said three contact elements to their outer positions.

2. The implement according to claim 1, wherein said predetermined angle is 90°, such that the longitudinal axis of said rod is precisely perpendicular to said plane of the target surface when said three contact points of the head are in contact with said plane of the target surface.

3. The implement according to claim 1, wherein the length of said rod from its distal end to its proximal end is many times the diameter of said circular array of three contact points of the head, thereby multiplying by said many times any deviation of said proximal end of the rod with respect to said predetermined angle.

4. The implement according to claim 1, wherein said implement further includes a tube enclosing said rod and having a proximal end at the proximal end of the rod; said tube having a larger diameter than said rod such that when said three contact points of the head at the distal end of the rod are in contact with said target surface, and said tube is manipulated such that the proximal end of the rod is centrally of the proximal end of the tube, said tube is oriented at said predetermined angle with respect to said plane of the target surface;

said tube being displaceable to either a first position wherein the distal end of its inner surface engages the outer surfaces of said contact elements to retain said contact elements in their inner positions, or to a second position wherein the digital end of its inner surface disengages from the outer surfaces of said contact elements to permit said contact elements to move to their outer positions.

5. The implement according to claim 4, wherein said three slits formed in the distal end of the head are of a Y-configuration and extend from the distal end of said head to points short of the proximal end of the head such that said three contact elements are three segmental elements outwardly displaceable to an expanded condition for defining said plane, or inwardly displaceable to a non-expanded condition to permit removal of said rod and head from said tube through the proximal end of the tube.

6. The implement according to claim 5, wherein the distal end of said rod is formed with a tapered configuration engageable with said three segmental elements of the head such that moving the rod in the distal direction with respect to said head forces said three segmental elements outwardly into engagement with the inner surface of the distal end of said tube.

7. The implement according to claim 6, wherein said rod is coupled to said head by a lost-motion connection permitting the rod to be moved in the proximal direction for a short distance with respect to said head before moving the head in the proximal direction, whereupon the inner surface of the distal end of the tube is engaged by the three segmental elements and moves them to their non-expanded condition to permit withdrawal of the rod and head from the tube via its proximal end.

8. The implement according to claim 7, wherein said lost-motion connection includes a pin fixed to said head moveable within a recess formed in said rod.

9. The implement according to claim 4, wherein said tube is dimensioned to receive a drill bit after the tube has been oriented by said rod and the rod and head removed from the tube, such that the tube serves as a drill guide for the drill bit.

10. The implement according to claim 4, wherein said tube is part of a surgical tool for cutting a plug of bone tissue from a bone at a donor site at said predetermined angle with respect to said bone.

11. A surgical implement comprising:
a surgical tool including a tube to be oriented at a predetermined angle with respect to a plane of a target surface to be engaged by the tool;
a rod located within said tube and of smaller outer diameter than the inner diameter of said tube; said rod having a longitudinal axis coaxial with that of said tube, a distal end to be disposed within the end of the said tube to engage the target surface, and a proximal end to project outwardly of the opposite end of the said tube;
and a head coupled to the distal end of said rod;
said head being formed with three contact elements arrayed in a circular array around said longitudinal axis and radially displaceable from inner positions to outer positions with respect to each other and to said longitudinal axis such that when in their outer positions, their tips are in contact with the target surface at three contact points which define a plane on the target surface at said predetermined angle to said longitudinal axis of the rod;
said contact elements being formed by three slits extending axially through the distal end of the head for a sufficient distance to enable the contact elements to be elastically deformed to said inner and outer positions;
said tube being displaceable to either a first position wherein the distal end of its inner surface engages the outer surfaces of said contact elements to retain said contact elements in their inner positions, or to a second position wherein the digital end of its inner surface disengages from the outer surfaces of said contact elements to permit said contact elements to move to their outer positions;
said rod being coupled to said head so as to be displaceable with respect thereto to radially displace said three contact elements to their outer positions.

12. The surgical implement according to claim 11, wherein said predetermined angle is 90°, such that the longitudinal axis of said tube is precisely perpendicular to the plane of said target surface when said three contact points of the head are in contact with said plane of the target surface.

13. The surgical implement according to claim 11, wherein the length of said rod from the distal end to its proximal end is many times the diameter of said circular array of three contact points, thereby multiplying by said many times any deviation of said surgical tool with respect to said predetermined angle.

14. The implement according to claim 11, wherein said three slits formed in the distal end of the head are of a Y-configuration and extend from the distal end of said head to points short of the proximal end of the head such that said three contact elements are three segmental elements outwardly displaceable to an expanded condition for defining said plane, or inwardly displaceable to a non-expanded condition to permit removal of said rod and head from said tube through the proximal end of the tube.

15. The implement according to claim 14, wherein said three segmental elements are defined by three axially-extending slits formed in the distal end of said head; said slits intersecting at the longitudinal axis of said rod such that said three segmental elements are elastically deformable to their expanded and non-expanded conditions.

16. The implement according to claim 14, wherein said tube is dimensioned to receive a drill bit after the tube has been oriented by said rod and the rod and head removed from the tube, such that the tube serves as a drill guide for the drill bit.

17. The implement according to claim 14, wherein said surgical tool includes a cutting section having a sharp cutting edge at its distal end, and a transparent section inwardly of said cutting section into which the plug of bone tissue may be moved to permit viewing the plug when the surgical tool is used for implanting the plug into the bore at the recipient site.

18. The implement according to claim 17, wherein said transparent section is integrally formed with said surgical tool, and said cutter section is in a separate unit receivable around said transparent section and having a quick-coupling for coupling same to said surgical tool with its sharp cutting edge located distally of the transparent section.

* * * * *